United States Patent
Magno et al.

(10) Patent No.: US 11,723,638 B2
(45) Date of Patent: Aug. 15, 2023

(54) CURVED BLADE FLEX WRAP WITH SEAL LINING

(71) Applicant: GYRUS ACMI, INC., Southborough, MA (US)

(72) Inventors: Joey Magno, Cordova, TN (US); Reid M. Anderson, Lakeland, TN (US); Canh S. Ly, Cordova, TN (US)

(73) Assignee: Gyrus ACMI, Inc., Westborough, MA (US)

( * ) Notice: Subject to any disclaimer, the term of this patent is extended or adjusted under 35 U.S.C. 154(b) by 271 days.

(21) Appl. No.: 17/017,956

(22) Filed: Sep. 11, 2020

(65) Prior Publication Data

US 2021/0100542 A1   Apr. 8, 2021

Related U.S. Application Data

(60) Provisional application No. 62/910,583, filed on Oct. 4, 2019, provisional application No. 62/994,969, filed on Mar. 26, 2020.

(51) Int. Cl.
| | |
|---|---|
| *A61B 17/00* | (2006.01) |
| *A61B 17/16* | (2006.01) |
| *A61B 17/32* | (2006.01) |
| *F16B 7/04* | (2006.01) |

(52) U.S. Cl.
CPC .... *A61B 17/00234* (2013.01); *A61B 17/1631* (2013.01); *A61B 17/32* (2013.01); *A61B 2017/00305* (2013.01); *A61B 2017/00526* (2013.01)

(58) Field of Classification Search
CPC ........ A61B 17/00305; A61B 17/00314; A61B 17/1631; A61B 17/32; F16B 7/0406; F16B 7/0413
See application file for complete search history.

(56) References Cited

U.S. PATENT DOCUMENTS

| | | | |
|---|---|---|---|
| 5,149,149 A * | 9/1992 | Wu | F16B 7/0413 403/348 |
| 5,286,253 A | 2/1994 | Fucci | |
| 5,322,505 A | 6/1994 | Krause et al. | |
| 5,620,447 A * | 4/1997 | Smith | A61B 17/32002 606/180 |
| 5,833,692 A | 11/1998 | Cesarini et al. | |
| 5,921,956 A * | 7/1999 | Grinberg | A61B 17/32002 604/95.01 |
| 5,922,003 A * | 7/1999 | Anctil | A61B 17/32002 464/181 |
| 6,620,180 B1 * | 9/2003 | Bays | A61B 17/32002 606/171 |
| 7,338,495 B2 | 3/2008 | Adams | |
| 8,721,826 B2 | 5/2014 | Hart et al. | |

(Continued)

*Primary Examiner* — Nicholas W Woodall
(74) *Attorney, Agent, or Firm* — Schwegman Lundberg & Woessner, P.A.

(57) ABSTRACT

A surgical device for cutting bone or tissue in a patient can include a cutting blade having a rigid portion, a flexible portion, and a liner to provide a seal to the flexible portion. The blade has an outer member and an inner member disposed within a lumen of the outer member. The inner member has a rigid portion and a flexible portion. The liner can be disposed within a lumen of the inner member and can engage the rigid portion such as to retain the liner adjacent to the flexible portion of the inner member.

13 Claims, 10 Drawing Sheets

(56) References Cited

U.S. PATENT DOCUMENTS

| | | |
|---|---|---|
| 9,308,013 B2 | 4/2016 | Casey et al. |
| 10,022,144 B2 * | 7/2018 | Nguyen ......... A61B 17/320783 |
| 10,166,013 B2 | 1/2019 | Nguyen et al. |
| 10,206,706 B2 * | 2/2019 | Nguyen ............. A61B 17/3205 |
| 2002/0038129 A1 * | 3/2002 | Peters .............. A61B 17/32002 |
| | | 606/167 |
| 2015/0374211 A1 * | 12/2015 | Smith ................ A61B 17/3421 |
| | | 600/114 |
| 2020/0367914 A1 * | 11/2020 | McGillicuddy .... A61B 17/1631 |

* cited by examiner

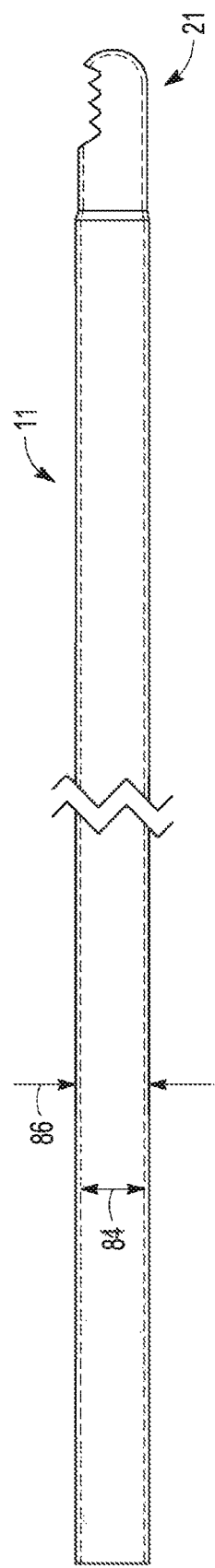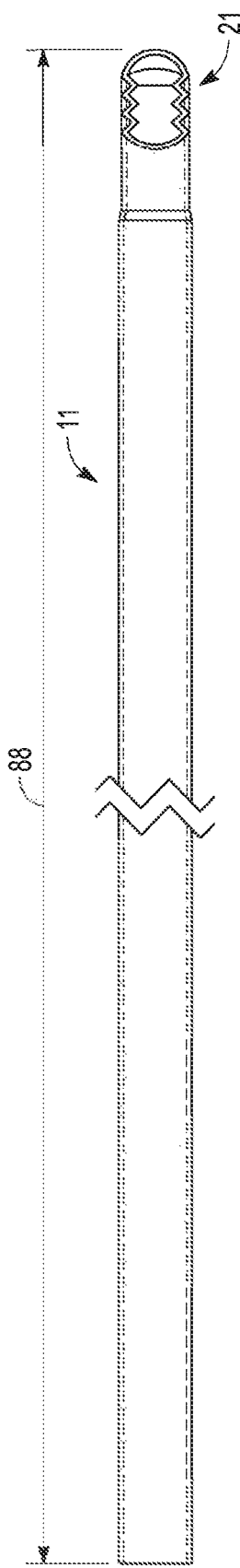
FIG. 6
FIG. 7

CURVED BLADE FLEX WRAP WITH SEAL LINING

CROSS-REFERENCE TO RELATED APPLICATIONS

This application claims the benefit of priority to U.S. Provisional Patent Application Ser. No. 62/910,583 filed on Oct. 4, 2019, and also claims the benefit of priority to U.S. Provisional Patent Application Ser. No. 62/994,969 filed on Mar. 26, 2020, the contents of which are incorporated herein in their entireties.

TECHNICAL FIELD

This document pertains generally, but not by way of limitation, to surgical instruments and methods for the manufacture and use of such surgical instruments and, more particularly, to cutting instruments comprising a flexible portion for insertion through a curved path.

BACKGROUND

Various surgical devices have been developed for inserting into and through a curved lumen or other curved pathway in a body, for example as are described in U.S. Pat. Nos. 10,206,706; 10,166,013; 9,308,013; 8,721,826; 7,338,495, 5,833,692; 5,322,505; and 5,286,253. These surgical devices may include a flexible portion configured to bend or flex during passage through the lumen or other pathway in the body.

OVERVIEW

The present technology relates to devices for cutting tissue in a body. A cutting device can include a generally tubular member. The tubular member can include a blade portion, a rigid portion, a flexible portion between the blade portion and the rigid portion and, and a liner disposed within the flexible portion of the cutting device. The rigid portion can be disposed at the proximal end of the cutting device. The blade portion can include one or more cutting windows and one or more cutting elements or cutting surfaces such as disposed at the distal end of the device. The flexible portion can include one or more strips of a flexible material, such as can be wound or wrapped around an axis of the tubular member in an intermediate region between the blade portion and the connecting or rigid portion. By providing a liner to the flexible portion of the cutting device, a seal is formed. The seal may help reduce loss of suction and may help inhibit or prevent compromised cutting performance and/or failure of the cutting device during use.

The following aspects and discussion illustrate various configurations of the disclosed device and methods.

Aspect 1 can include an outer member including a cutting window, an inner member disposed at least partially within the outer member, and a liner. The outer member can include a tube that defines a first lumen. The inner member can extend through at least a portion of the first lumen defined by the outer member. The inner member may include a cutting surface and at least two portions, each of the two portions having a different flexibility. For instance, the inner member may comprise a rigid portion and a flexible portion, the flexible portion being more flexible than the rigid portion. The liner may be configured to be disposed within the inner member. The inner member can define a second lumen and the liner can extend through at least a portion of the second lumen. The liner may include a locking feature configured to engage the rigid portion of the inner member, such that at least one end of the liner is retained at a predetermined position within the lumen.

Aspect 2 can include, use, or can optionally be combined with the subject matter of Aspect 1, or any one or any combination of elements of Aspect 1, to optionally include or use a locking feature comprising an end wall of the liner.

Aspect 3 can include, use, or can optionally be combined with the subject matter of Aspects 1 or 2, or any one or any combination of elements of Aspects 1 or 2, to optionally include or use a locking feature comprising a flared region of a liner outer wall or a projection extending from the liner outer wall.

Aspect 4 can include, use, or can optionally be combined with the subject matter of Aspects 1 through 3, or any one or any combination of elements of Aspects 1 through 3, to optionally include or use an inner wall comprising a stop configured to engage the locking feature to retain the liner at the predetermined position.

Aspect 5 can include, use, or can optionally be combined with the subject matter of Aspect 4, or any one or any combination of elements of Aspect 4, to optionally include or use a stop disposed adjacent to a distal end of the at least one rigid portion.

Aspect 6 can include, use, or can optionally be combined with the subject matter of Aspects 4, or any one or any combination of elements of Aspect 4, to optionally include or use a stop disposed adjacent to a proximal end of the at least one rigid portion.

Aspect 7 can include, use, or can optionally be combined with the subject matter of Aspects 1 through 6, or any one or any combination of elements of Aspects 1 through 6, to optionally include or use a lumen of the inner member having a first inner diameter and a second inner diameter, different from the first inner diameter, and a locking feature configured to engage the inner wall at a transition between the first inner diameter and the second inner diameter.

Aspect 8 can include, use, or can optionally be combined with the subject matter of Aspects 1 through 7, or any one or any combination of elements of Aspects 1 through 7, to optionally include or use an inner wall having a first thickness and a second thickness, different from the first thickness, and the locking feature is configured to engage the inner wall at a transition between the first thickness and the second thickness of the inner wall.

Aspect 9 can include, use, or can optionally be combined with the subject matter of Aspects 1 through 8, or any one or any combination of elements of Aspects 1 through 8, to optionally include or use an at least one rigid portion having a first rigid portion and a second rigid portion axially spaced from the first rigid portion, and the locking feature having a first locking feature configured to engage the inner wall of the first rigid portion and a second locking feature configured to engage the inner wall of the second rigid portion.

Aspect 10 can include, use, or can optionally be combined with the subject matter of Aspects 1 through 9, or any one or any combination of elements of Aspects 1 through 9, to optionally include or use a locking feature configured to engage a recess or aperture in the inner wall of the at least one rigid portion.

Aspect 11 can include, use, or can optionally be combined with the subject matter of Aspects 1 through 10, or any one or any combination of elements of Aspects 1 through 10, optionally include or use an inner wall comprising a recess or aperture configured to engage the locking feature.

Aspect 12 can include, use, or can optionally be combined with the subject matter of Aspects 1 through 11, or any one or any combination of elements of Aspects 1 through 11, to optionally include or use an inner wall of the at least one rigid portion that extends perpendicular to a longitudinal axis of the inner member.

Aspect 13 can include, use, or can optionally be combined with the subject matter of Aspects 1 through 12, or any one or any combination of elements of Aspects 1 through 12, to optionally include or use a predetermined position that is adjacent to the at least one flexible portion.

Aspect 14 can include, use, or can optionally be combined with the subject matter of Aspects 1 through 13, or any one or any combination of elements of Aspects 1 through 13, to include or use a liner configured to engage an inner wall of the at least one rigid portion to form a seal between the liner and the inner member.

Aspect 15 can include, use, or can optionally be combined with the subject matter of Aspects 1 through 14, or any one or any combination of elements of Aspects 1 through 14, to optionally include or use a method of forming a surgical tool comprising a cutting window, a cutting surface and a flexible portion, the method comprising inserting a liner into a lumen of a first member comprising the cutting surface and inserting the first member into a lumen of a second member comprising a cutting window.

Aspect 16 can include, use, or can optionally be combined with the subject matter of Aspects 1 through 15, or any one or any combination of elements of Aspects 1 through 15, to optionally include or use a method in which the first member is inserted into the lumen of the second member after the liner is inserted into the lumen of the first member.

Aspect 17 can include, use, or can optionally be combined with the subject matter of Aspects 1 through 16, or any one or any combination of elements of Aspects 1 through 16, to optionally include or use a method further comprising applying a temperature greater than 25° C. to the liner after the liner is inserted into the lumen of the first member.

Aspect 18 can include, use, or can optionally be combined with the subject matter of Aspects 1 through 17, or any one or any combination of elements of Aspects 1 through 17, to optionally include or use a method further comprising applying a fluid to the liner after the liner is inserted into the lumen of the first member.

Aspect 19 can include, use, or can optionally be combined with the subject matter of Aspects 1 through 18, or any one or any combination of elements of Aspects 1 through 18, to optionally include or use a method further comprising applying a pressure to the liner after the liner is inserted into the lumen of the first member.

Aspect 20 can include, use, or can optionally be combined with the subject matter of Aspects 1 through 19, or any one or any combination of elements of Aspects 1 through 19, to optionally include or use a method in which the liner is cooled to a temperature below 25° C. before the liner is inserted into the lumen of the first member.

Aspect 21 can include or use any one or any combination of Aspects 1 through 20 or any one or any combination of elements of Aspects 1 through 20.

This overview is intended to provide a generalized summary of subject matter of the present patent application. It is not intended to provide an exclusive or exhaustive explanation of the invention. The detailed description is included to provide further information about the present patent application and the inventions disclosed herein.

BRIEF DESCRIPTION OF THE DRAWINGS

In the drawings, which are not necessarily drawn to scale, like numerals may describe similar components in different views. The drawings illustrate generally, by way of example, but not by way of limitation, various examples discussed in the present document.

FIG. 1A illustrates a curved blade connected to a handle in an example of a cutting device or system. FIG. 1B illustrates perspective views of a curved blade in a disassembled state, including a liner, an inner member, and an outer member.

FIG. 6 illustrates a side view of an outer member of a curved blade.

FIG. 7 illustrates a top view of an outer member of a curved blade.

DETAILED DESCRIPTION

Figure 1A:
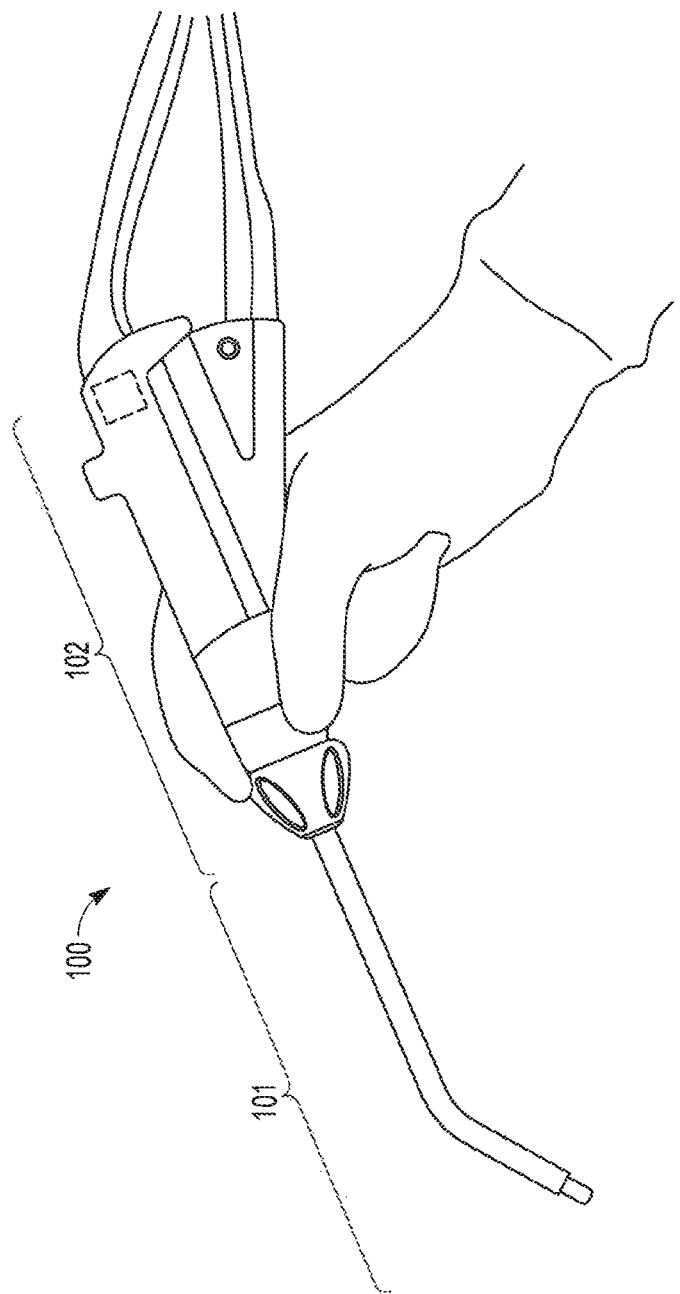
FIGS. 1A and 1B illustrate examples of a curved blade.

The present disclosure is directed to a surgical cutting device comprising a flexible portion and related combinations, systems and methods. The devices, apparatuses, combinations, systems, methods and techniques of the present application are not limited to any particular type of procedure or use. Indeed, the present devices, apparatuses, combinations, systems, methods and techniques can be utilized in any medical procedure that uses a cutting device.

A surgical device may include a flexible portion that may include a tubular structure that is formed of a material configured to flex during insertion or movement through a lumen or other pathway in a body. For example, without limitation, a surgical device may include a debrider, a burr, a rasp, a blade, a knife, a suction, a forceps, a probe, a curette, a cannula, a snare, a scope, or the like. It may be beneficial for the surgical device to be deformable, malleable, or configured to flex such that the surgical device can be manipulated through a passage or within cavity in a human or animal body that is not entirely straight, through a narrow passage, or around an obstruction in a passage or cavity, e.g., a nasal passage, a sinus passage, a laryngeal passage, a gastrointestinal passage, a kidney passage, a urogenital passage, or other narrow or tortuous passage in a body. To enhance flexing of the surgical device, the tubular structure may include a flexible material that is wrapped or wound around an axis of the tubular structure such as to help provide flexibility in one or more portions of the tubular structure. The flexible surgical device can be configured to provide cutting of tissue in or adjacent to the path of insertion or movement of the surgical device. The cutting may be provided by reciprocation, by oscillation or by rotation of a tubular structure that has a blade, serrations, teeth, burr, or one or more other cutting elements. A flexible cutting assembly can include an outer tubular structure. An inner tubular structure can be co-axially disposed within the outer tubular structure. The inner tubular structure can include one or more flexible regions. A cutting element or blade can be disposed at a distal end of the inner tubular structure. The cutting element or blade can be exposed from an opening at a distal end of the outer tubular structure such as to allow cutting of anatomical tissue at the surgical site when the inner tubular member is reciprocated, oscillated, or is rotated within the outer tubular member.

The flexible cutting device can also be configured to provide suction. Such suction can be useful to withdraw tissue that has been excised, such as to help provide for more efficient cutting by the surgical device. For example, the internal lumen of the inner tubular member can be used to provide suction to aspirate anatomical tissue, body or irrigation fluid, or both, such as through the lumen of the inner tubular structure. An annular gap between the internal diameter of the outer tubular structure and the external diameter of the inner tubular structure can provide another path such as for suction or as an irrigation passage to supply irrigation fluid to the surgical site. Cutting devices with a flexible portion can use one or more strips of material spirally wrapped or wound about an axis of the inner tubular structure such as to impart flexibility to the flexible portion. The flexible portion of the tubular structure may have a spiral construction, such as of a plurality of strips compiled into one or more than one combination of counter helical spirals. The construction of the strips and/or helical spiral arrangement of the strips may not be of a completely sealed construction. Sometimes, wrapped or wound flexible materials can tend to partially or fully unwind when rotated in a direction opposite their winding, resulting in gaps in the flexible tubular structure. A degradation or loss of suction can occur due to absence of a completely sealed construction of the flexible wrap material. A loss of suction can also occur due to gaps that may exist or form in the flexible wrap material. The loss of suction can cause the device to clog when aspirating cut tissue, leading to inefficient cutting, device failure, or both.

There is a need for a flexible tubular surgical device capable of maintaining suction when transmitting torque, such as can be addressed by a flexible tubular cutting device that has a sealed flexible wrap portion to enhance suction during use, such as described herein. There is also a need for a flexible cutting device that allows a curved cutting element or blade to bend around a radius such as while in an oscillating mode.

Figure 1B:
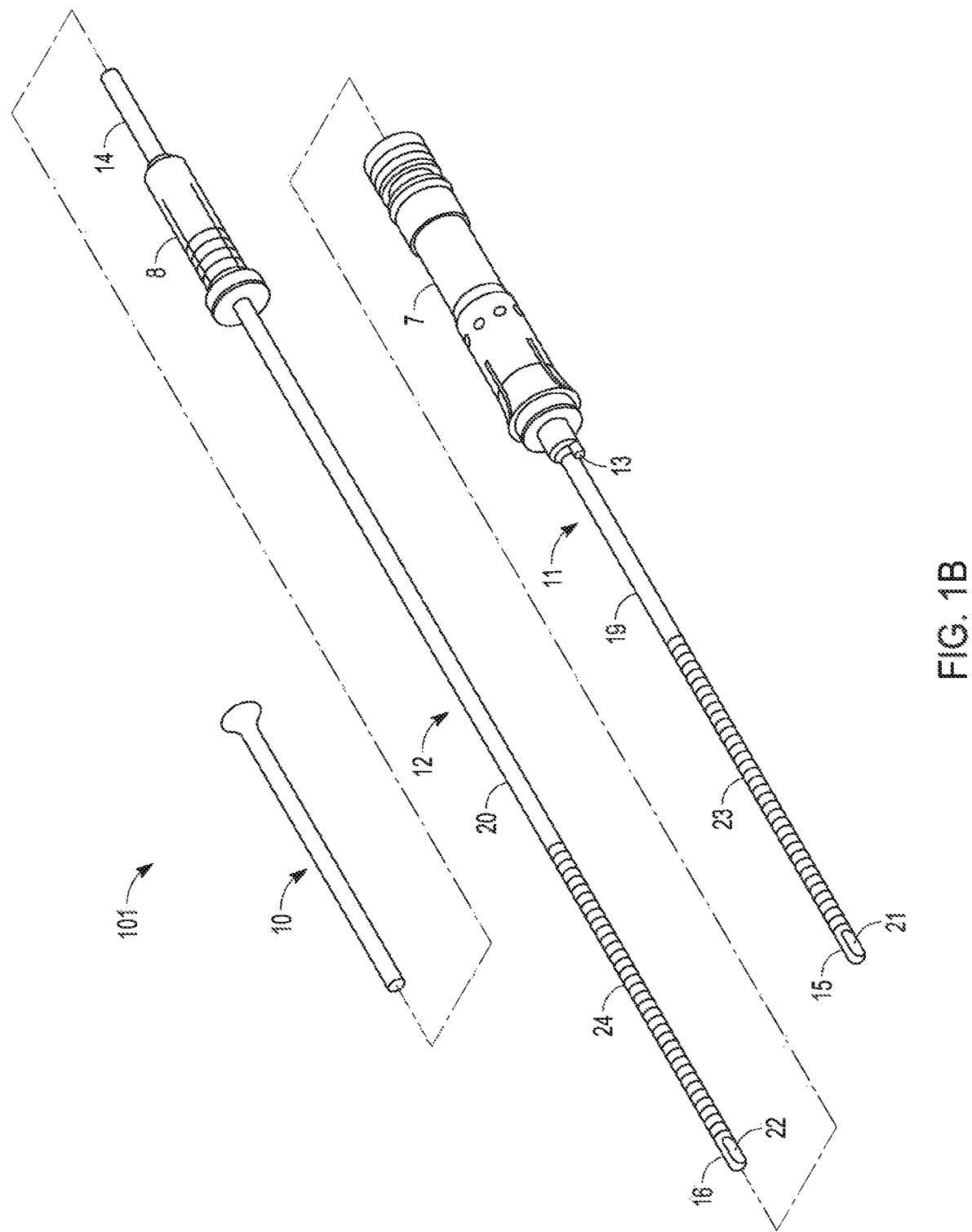

FIGS. 1A and 1B illustrate examples of a curved blade 101 that can be used as part of a combination, assembly, kit, or system 100 such as for shaving, cutting, resecting, abrading and/or removing tissue, bone and/or bodily fluids from a surgical site. The curved blade 101 can include at least one relatively more rigid portion 19, 20, 21, 22, and at least one relatively more flexible portion, such as one of 23 or 24. The curved blade 101 can comprise a liner 10, an outer member 11 such as extending between a proximal end 13 and a distal end 15, and an inner member 12 such as extending between a proximal end 14 and a distal end 16. The outer member 11 can be configured with a connector 7 adjacent to the proximal end 13. The inner member 12 can be configured with a connector 8 adjacent to the proximal end 14. The connector 7 and the connector 8 can be configured to detachably couple the inner member 12 to the outer member 11. For example, the connector 8 and the connector 7 can be configured to detachably couple the inner member 12 to the outer member 11 such that the inner member 12 can be reciprocated, rotated or oscillated relative to the outer member 11. The connector 7 and the connector 8 can be configured to detachably couple the curved blade 101 to a tool handle 102. For example, the connector 7 and the connector 8 can be configured to detachably couple the curved blade 101 to a tool handle 102 (illustrated in FIG. 1A) such that the outer member 11 of the curved blade 101 is stationary with respect to the tool handle 102. The outer member connector 7 and the inner member connector 8 can be configured to detachably couple the curved blade 101 to a tool handle 102 such that the inner member 12 of the curved blade 101 can reciprocate, rotate or oscillate relative to the tool handle 102, relative to the outer member 11, or relative to both the tool handle 102 and the outer member 11. The outer member connector 7 and the inner member connector 8 can be configured to detachably couple the curved blade 101 to a tool handle 102 such that the outer member 11 can reciprocate, rotate or oscillate relative to the tool handle 102, relative to the inner member 12, or relative to both the tool handle 102 and the inner member 12.

Any means suitable for fixedly or detachably coupling an inner member to an outer member can be used to couple inner member 12 to outer member 11. Any connector suitable for detachably coupling a cutting device to a tool handle 102 can be used to detachably couple the curved blade 101 to a tool handle 102. Some examples of connectors for coupling a blade to a tool handle are described in U.S. Pat. Nos. 5,286,253; 7,338,495; and 9,308,103. For example, a connector such as described in U.S. Pat. No. 9,308,103, which is incorporated herein by this reference, can be used to detachably couple the inner member 12 to the outer member 11, and/or to detachably couple the curved blade 101 to a tool handle 102. A curved blade 101 can be detachably coupled to a tool handle 102 such that the inner member 12 of the curved blade 101 can reciprocate, rotate or oscillate with respect to the outer member 11, with respect to the tool handle 102, or with respect to both outer member 11 and the tool handle 102. The outer member 11 of the curved blade 101 can be detachably coupled to a tool handle 102 such that the outer member 11 can reciprocate, rotate or oscillate with respect to the tool handle 102, with respect to the inner member 12, or with respect to both the tool handle 102 and the inner member 12.

Figure 8:
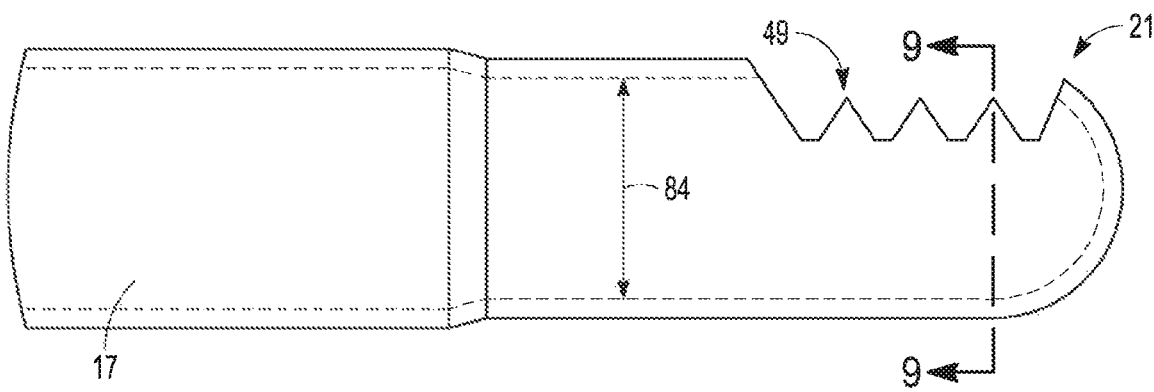
FIG. 8 illustrates a detailed view of a blade portion of an outer member of the curved blade shown in FIG. 6.
Figure 9:
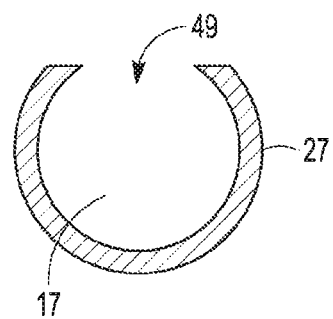
FIG. 9 illustrates cross-sectional view at feature (9-9) of the outer member of the curved blade shown in FIG. 8.
Figure 10:
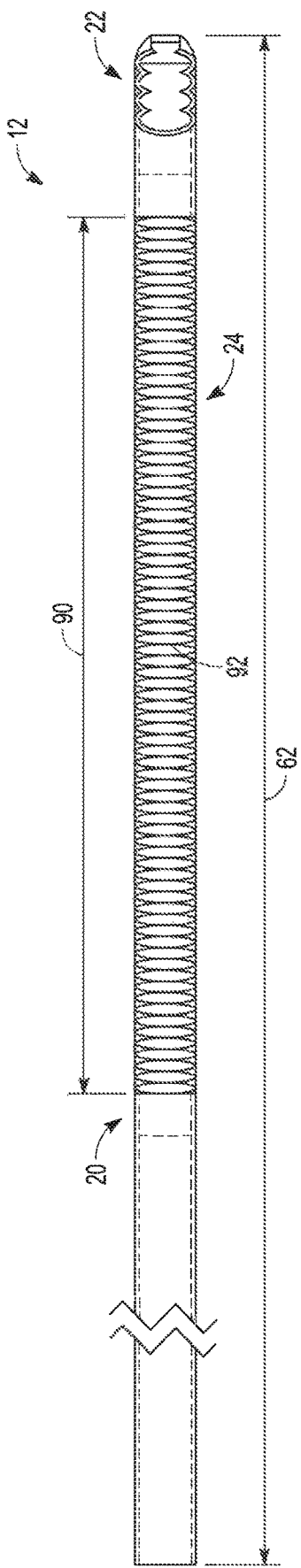
FIG. 10 illustrates a top view of an inner member of a curved blade.
Figure 11:
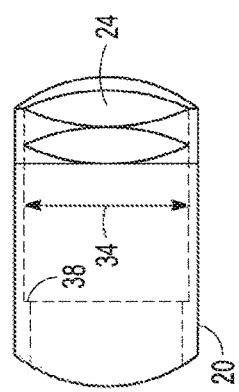
FIG. 11 illustrates an exploded view of a junction between a rigid portion and a flexible portion of the inner member of the curved blade shown in FIG. 10.
Figure 12:
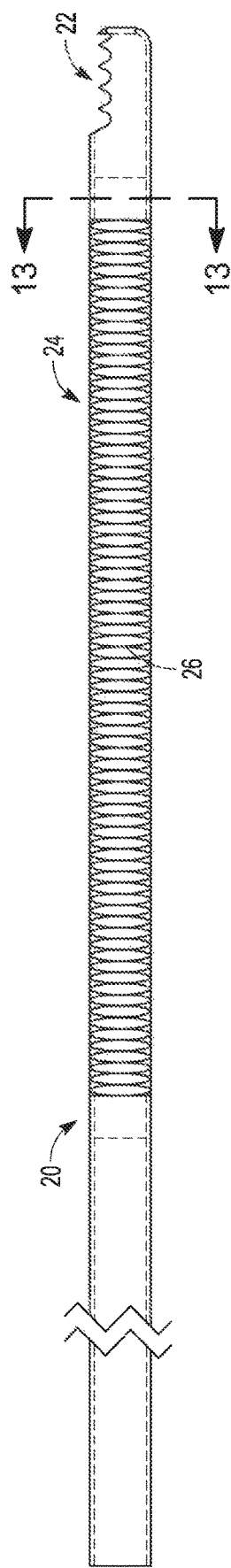
FIG. 12 illustrates side view of an inner member of a curved blade.

The curved blade 101 can have a generally tubular structure. As illustrated in FIGS. 1B, 6, and 7, an outer member 11 can extend a length 88 between a proximal end 13 and a distal end 15. As shown in FIGS. 8 and 9, an outer member 11 can comprise a lumen 17. The outer member 11 can have an outer diameter 86 and an inner diameter 84 (FIGS. 6 and 8). An outer member 11 can have any length 88, any outer diameter 86 and any inner diameter 84. In one aspect, an outer member 11 can have a length 88 between about 10 cm and about 1 mm. In certain aspects, an outer member 11 can have a length 88 between about 10 mm to about 1 mm. In a preferred aspect, an outer member can have a length 88 between about 5 mm to about 1 mm. In one aspect, an outer member 11 can have an outer diameter 86 between about 10 cm and about 0.1 mm. In an aspect, an outer member 11 can have an outer diameter 86 between about 10 mm and about 0.1 mm. In a preferred aspect, an outer member 11 can have an outer diameter 86 between about 0.5 mm to about 0.1 mm. In one aspect, an outer member 11 can have an inner diameter 84 between about 10 cm and about 0.01 mm. In an aspect, an outer member 11 can have an inner diameter 84 between about 10 mm and about 0.01 mm. In a preferred aspect, an outer member 11 can have an inner diameter 84 between about 5 mm and about 0.01 mm. In certain preferred aspects, an outer member 11 can have a length 88 and an inner diameter 84 configured to receive an inner member 12 as described below.

Figure 2:
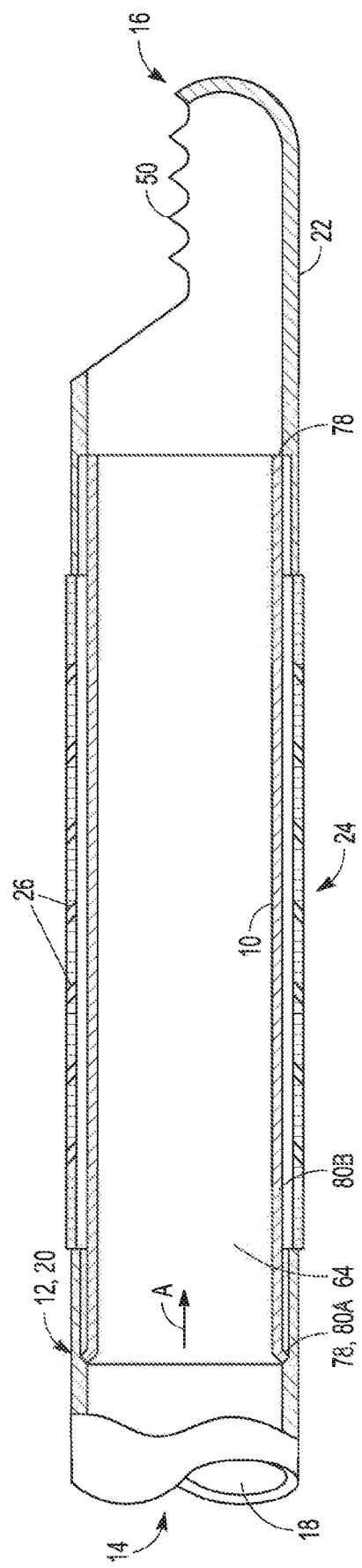
FIG. 2 illustrates a cross-sectional view of an inner member and a liner of a curved blade, in an assembled configuration.
Figure 3:
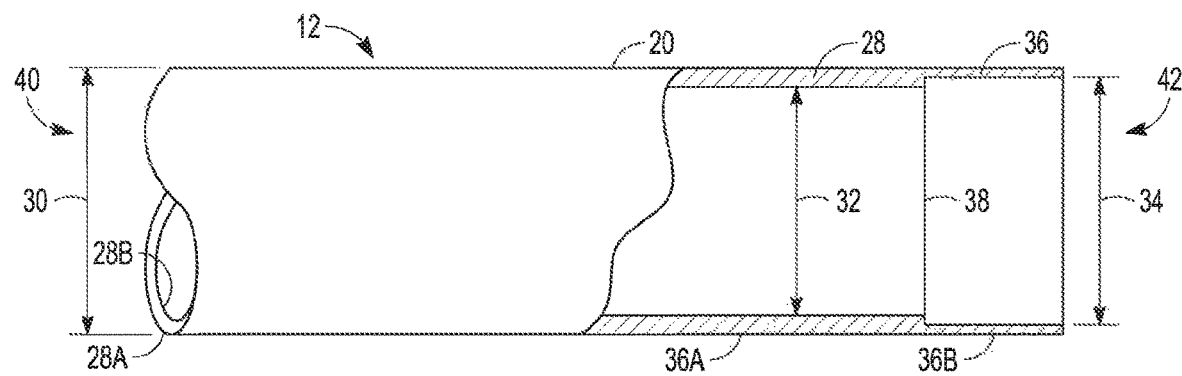
FIG. 3 illustrates a cross-sectional view of a rigid portion of an inner member of a curved blade.
Figure 4:
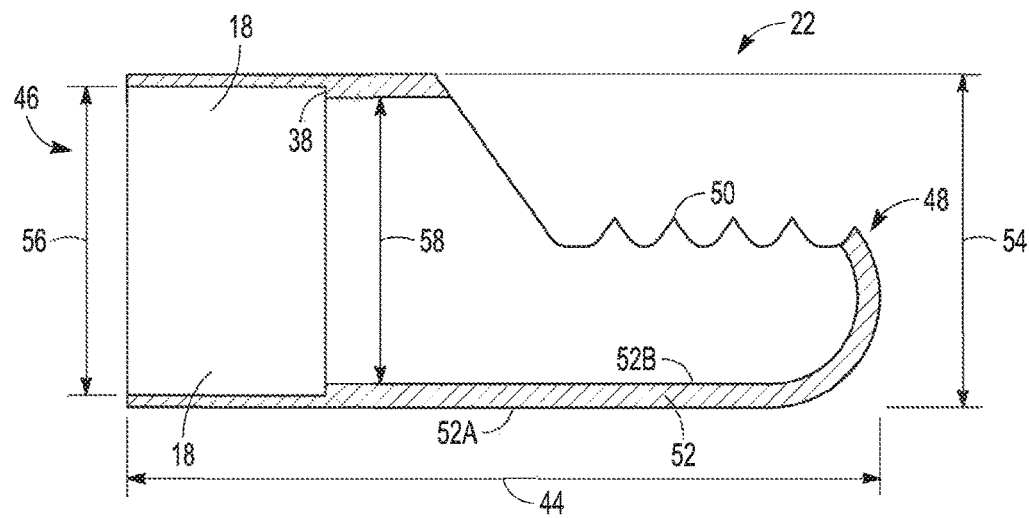
FIG. 4 illustrates a cross-sectional view of a blade portion of an inner member of a curved blade.
Figure 5:
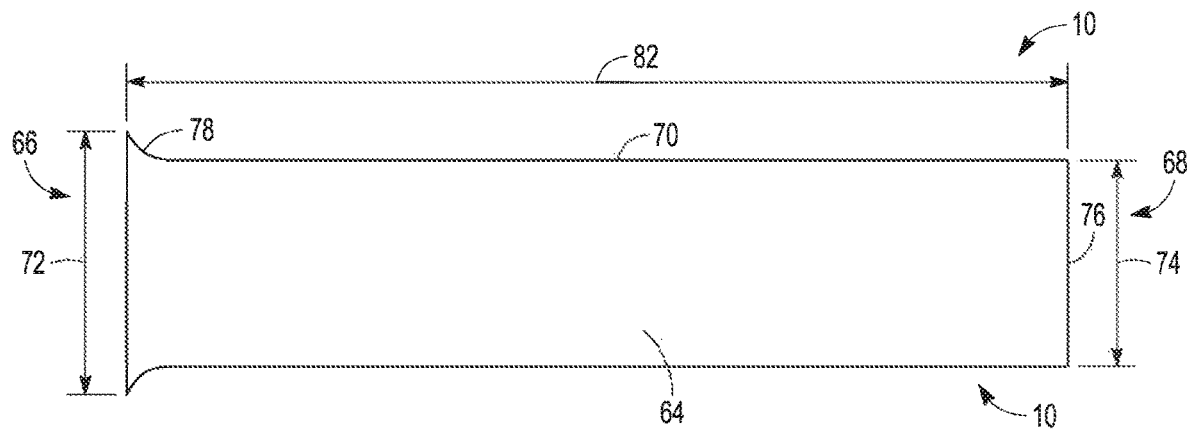
FIG. 5 illustrates a side view of a liner of a curved blade.
Figure 13:
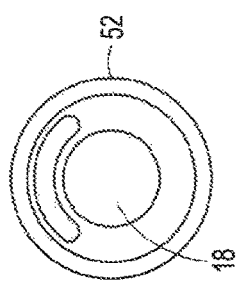
FIG. 13 illustrates a cross-sectional view at feature (13-13) of the inner member of a curved blade shown in FIG. 12.
Figure 14:
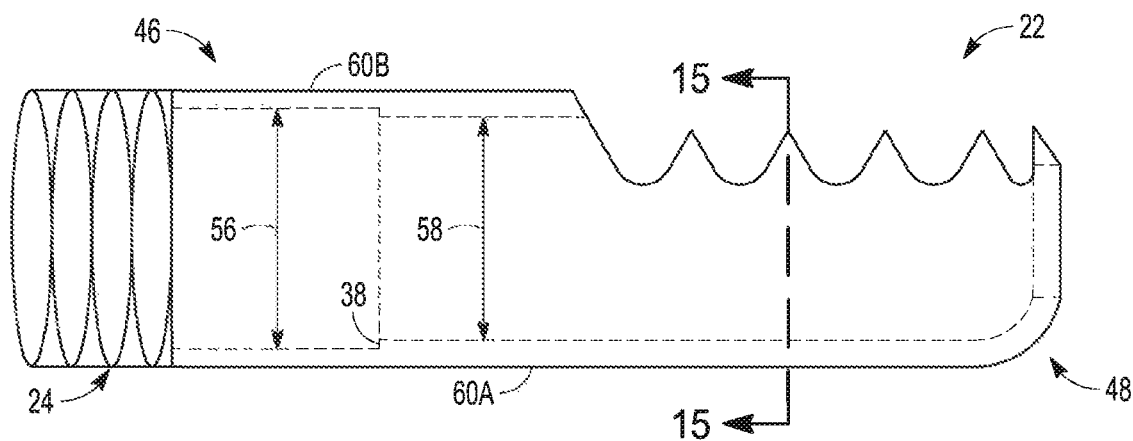
FIG. 14 illustrates a blade portion of the inner member of a curved blade shown in FIG. 12.
Figure 15:
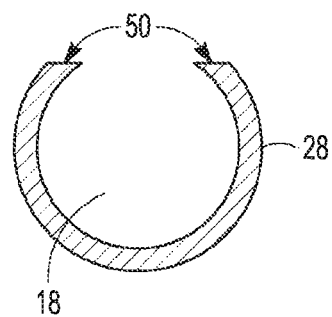
FIG. 15 illustrates a cross-sectional view at feature (15-15) of the inner tube of a curved blade shown in FIG. 14.

An outer member 11 can comprise a lumen 17 configured to receive an inner member 12 such that in an assembled configuration the inner member 12 can be co-axially disposed within the outer member 11. As illustrated in FIGS. 1, 10, 11 and 12, an inner member 12 can extend a length 62 between a proximal end 14 and a distal end 16. As shown in FIGS. 2, 13 and 15, in one aspect an inner member 12 can comprise a lumen 18. As illustrated in FIGS. 3, 4, and 14, in an aspect, an inner member 12 have an outer diameter 30, 54 and an inner diameter 32, 34, 56, 58. An inner member 12 can have any length 62, any outer diameter 30, 54, and any inner diameter 32, 34, 56, 58. In one aspect, an inner member 12 can have a length 62 between about 20 cm and about 1 mm. In a preferred aspect, an inner member 12 can have a length 62 between about 20 mm to about 1 mm. In one aspect, an inner member 12 can have a length 62 that is equal to the length 88 of an outer member 11. In an aspect, an inner member 12 can have a length 62 that is greater than a length 88 of an outer member 11. In one aspect, an inner member 12 can have an outer diameter 30, 54 between about 10 cm and about 0.01 mm. In an aspect, an inner member 12 can have an outer diameter 30, 54 between about 10 mm and about 0.01 mm. In a preferred aspect, an inner member 12 can have an outer diameter 30, 54 between about 0.5 mm to about 0.01 mm. In one aspect, an inner member 12 can have an inner diameter 32, 34, 56, 58 between about 10 cm and about 0.01 mm. In an aspect, an inner member 12 can have an inner diameter between about 10 mm and about 0.01 mm. In a preferred aspect, an inner member 12 can have an inner diameter 32, 34, 56, 58 between about 5 mm and about 0.01 mm. In a preferred aspect, an inner member 12 can have an outer diameter 30, 54 that is configured to be receivable in a lumen 17 of an outer member 11. In one aspect, an inner member 12 can have an outer diameter 30, 54 that is less than the inner diameter 84 of the outer member 11.

The inner member 12 can comprise a lumen 18 configured to receive a liner 10 (FIGS. 1, 2, 5, and 16) such that in an assembled configuration the liner 10 is co-axially disposed with the inner member 12. The liner 10 can comprise a length 82, an outer diameter 72, 74 and an inner lumen 64 diameter. The liner 10 can have any length 82, any inner lumen 64 diameter, and any outer diameter 72, 74. In an aspect, a liner can have a length 82 between about 10 cm and about 0.1 min. In an aspect, a liner 10 can have a length 82 between about 10 mm and about 0.1 mm. In a preferred aspect, a liner 10 can have a length 82 between about 5 mm and about 0.1 mm. The liner 10 can have a length 82 and an outer diameter 72, 74 such that the liner 10 can be configured to be entirely received within a lumen 18 of an inner member 12. The liner 10 can have a length 82 that is substantially the same as the length 62 of the inner member 12. The liner 10 can have a length 82 that is less than the length 62 of the inner member 12 such that when the liner 10 is inserted into the inner member 12 (as described in detail below) the liner 10 does not contact a cutting surface 50 of the inner member 12 and is not exposed by a cutting window 49 of outer member 11.

The liner 10 can have a length 82 equal to or greater than a length of a flexible portion 24 (such as described in more detail below) of an inner member 12 of a curved blade 101. In an aspect, a liner 10 can have an outer diameter 72, 74 between about 10 cm and about 0.01 mm. In an aspect, a liner 10 can have an outer diameter 72, 74 between about 10 mm and about 0.01 mm. In a preferred aspect, a liner 10 can have an outer diameter 72, 74 between about 0.5 mm to about 0.01 mm. In an aspect, a liner 10 can have an inner diameter or lumen 64 diameter between about 10 cm and about 0.01 mm. In an aspect, a liner 10 can have a lumen 64 diameter between about 10 mm and about 0.01 mm. In a preferred aspect, a liner 10 can have a lumen 64 diameter between about 5 mm and about 0.01 mm.

An inner member 12 can have an outer diameter 30, 54 and an inner diameter 32, 34, 56, 58. As illustrated in FIGS. 2, 3, 4, and 14, the inner member 12 can have a larger inner diameter 32, 34, 56 than an outer diameter 72, 74 of a liner 10. For example, an inner member 12 can have a larger inner diameter 32, 34, 56 than an outer diameter 72, 74 of the liner 10 such as allowing for insertion of the liner 10 within the inner member 12. Portions of each of the liner 10, inner member 12, and outer member 11 can comprise generally tubular structures configured such that the liner 10 can be disposed within a lumen 18 of the inner member 12, and the inner member 12 can be disposed within a lumen 17 of the outer member 11, such as to provide a fully assembled configuration in which the liner 10, the inner member 12, and the outer member 11 can be co-axially disposed relative to one another as illustrated in FIG. 1B. In a fully assembled configuration, a lumen 64 of the liner 10 can cooperate with a lumen 18 of the inner member 12 such as to provide a fluid passage through the curved blade 101.

As shown in FIGS. 1, 2, 10, 11, and 12, a curved blade 101 can comprise at least one rigid portion 19, 20, 21, 22, and at least one flexible portion such as 23 or 24. A flexible portion can be radially, symmetrically bendable about a longitudinal axis A of the curved blade 101. The flexible portion 23 or 24 can be bent in any direction relative to the longitudinal axis (e.g., up, down, left, right, and in any and all directions in between). The flexible portion 23 or 24 can be bent to any degree relative to the longitudinal axis A, e.g., between 0° and 180° relative to the longitudinal axis. A rigid portion can be rigid or inflexible or can have a flexibility that is less than the flexibility of a flexible portion of the curved blade 101. In an example in which a curved blade 101 has two or more flexible portions 23, 24, each one of the flexible portions 23, 24 can have a flexibility that is the same as or that is different from the flexibility of the other flexible portions. In an example, a curved blade 101 can have two or more flexible portions, each one of the flexible portions can flex independently of the other flexible portions. In FIGS. 1, 4, 10, 12 and 16, a rigid portion 19, 20, 21, 22 can be connected to a flexible portion 23, 24 of the curved blade 101. The rigid portion 21, 22 can comprise a blade, serrations, teeth, burr, or other cutting elements. An outer member 11 can comprise a rigid portion 19 such as adjacent to a proximal end 13 of the outer member 11. An outer member 11 can comprise a rigid portion 21 such as adjacent to the distal end 15 of the outer member 11. In FIGS. 6 and 7, an outer member 11 can comprise a rigid portion 19, 21 that can extend the entire length of the outer member 11 between the proximal end 13 and the distal end 15, such that the outer member 11 does not have a flexible portion. An inner member 12 can comprise a rigid portion 20 adjacent to the proximal end 14 of the inner member 12. The inner member 12 can comprise a rigid portion 22 adjacent to the distal end 16 of the inner member 12. A first rigid portion 19, 20 adjacent to a proximal end 13, 14 of the curved blade 101 can extend distally toward a second rigid portion 21, 22 adjacent to the distal end 15, 16 of the curved blade 101 that can include a rigid portion 21, 22. A rigid portion 21 of an outer member 11 can comprise a cutting window 49. A rigid portion 22 of an inner member 12 can comprise a cutting surface 50. A rigid portion 19, 20, 21, 22 of a curved blade 101 can be formed of a rigid or in-flexible material or a material having less flexibility than a flexible portion 23, 24 of the curved blade 101. A rigid portion 19, 20, 21, 22 of a curved blade 101 can comprise a metal, a polymer, a ceramic, a carbon allotrope, e.g., graphene, or a combination of these.

In FIGS. 2, 3, 4 and 14, a lumen 18 of the inner member 12 can comprise one or a plurality of inner diameters 32, 34, 56, 58. An inner member 12 can comprise a wall 28, 52 having one or a plurality of thicknesses 36A, 36B, 60A, 60B. A plurality of inner diameters 32, 34, 56, 58 or a plurality of wall thicknesses 36A, 36B, 60A, 60B can form, or provide a location for forming, a detent or stop 38 configured to engage a locking feature 78 of a liner 10, such as described in detail below. A change in the inner diameter of a rigid portion 20, 22 and/or a change in wall thickness of a rigid portion 20, 22 can form, or provide a location or predetermined position for receiving a liner 10 within the lumen 18 of the inner member 12. In one aspect, an inner diameter 32, 34, 56, 58 of an inner member 12 can be between about 0.001 mm and about 10 mm. In a preferred aspect, an inner diameter 32, 34, 56, 58 can be between about 0.001 mm and about 0.1 mm. In an aspect, a wall thickness 36A, 36B, 60A, 60B of an inner member 12 can be between about 0.001 mm and about 10 mm. In a preferred aspect, a wall thickness 36A, 36B, 60A, 60B of an inner member 12 can be between about 0.001 mm and about 1 mm. The inner member 12 can comprise a rigid portion 20, 22 having an outer wall 28A, 52A and an outer diameter 30, 54. An inner wall 28B, 52B of the rigid portion 20, 22 can define the lumen 18. The lumen 18 can have a first inner diameter 32, 56. The lumen 18 can have a second inner diameter 34, 58. A rigid portion 20, 22 can have a first inner diameter 32, 56 and a second inner diameter 34, 58 different from the first inner diameter 32, 56. An inner wall 28B, 52B of the rigid portion 20, 22 can define a lumen 18 having a first inner diameter 32, 56 adjacent to a proximal end 40, 46 of the at least one rigid portion 20, 22. An inner wall 28B, 52B of the rigid portion 20, 22 can define a lumen 18 having a second inner diameter 34, 58 adjacent to a distal end 42, 48 of the rigid portion 20, 22. The second inner diameter 34, 58 can be different from the first inner diameter 34, 56. For example, a second inner diameter 34 of the rigid portion 20 can be greater than a first inner diameter 32 of the rigid portion 20. Or, for example, a second inner diameter 58 of the rigid portion 22 can be less than a first inner diameter 56 of the rigid portion 22.

An inner wall 28B, 52B of a rigid portion 20, 22 of a curved blade 101 can form or include a detent or stop 38 configured to retain a liner 10 within the lumen 18 of the inner member 12. A stop 38 can be formed when an inner diameter 32, 34, 56, 58 of the inner member 12 is less than an outer diameter 72, 74 of the liner 10. A stop 38 can be formed in a region where there is friction between the inner wall 28B, 52B of the inner member 12 and a liner wall 70, 76. A stop 38 can be disposed at a transition in the inner diameter 32, 34, 56, 58 of the inner member 12. The stop 38 can comprise a transition in the inner diameter 32, 34, 56, 58 of the inner member 12. The stop 38 can comprise a transition between a first inner diameter 32, 56 and a second inner diameter 34, 58 of the inner member 12. The stop 38 can be disposed at a transition in a thickness of an inner wall 28B, 52B. The stop 38 can comprise a transition in the thickness 36A, 36B, 60A, 60B of the inner wall 28B, 52B. The stop 38 can comprise a transition between the first thickness 36A, 60A of the inner wall 28B, 52B and the second thickness 36B, 60B of the inner wall 28B, 52B that is different from the first thickness. The stop 38 can comprise a transition between the first thickness 36A, 60A of the inner wall 28B, 52B and the second thickness 36B, 60B of the inner wall 28B, 52B that is less than the first thickness 36A, 60A. The stop 38 can comprise a transition between the first thickness 36A, 60A of the inner wall 28B, 52B and the second thickness 36B, 60B of the inner wall 28B, 52B that is greater than the first thickness 36A, 60A.

The stop 38 can be disposed adjacent to a distal end 42, 48 of a rigid portion 20, 22. The stop 38 can be disposed adjacent to a proximal end 40, 46 of a rigid portion 20, 22. The stop 38 can comprise one or more projections extending from the inner wall 28B, 52B. The stop 38 can comprise one or more apertures or recesses formed in the inner wall 28B, 52B. The stop 38 can extend around all or a portion of the circumference of the inner wall 28B, 52B. The stop 38 can be disposed at one or a plurality of discrete locations around the circumference or other periphery of the inner wall 28B, 52B. The stop 38 can comprise an annular ledge or abutment formed by the inner wall 28B, 52B of the rigid portion 20, 22. The stop 38 can comprise an annular ledge or abutment formed around all or only a portion of the circumference or other periphery of the inner wall 28B, 52B. The stop 38 can be configured to limit movement of a liner 10 toward a proximal end 40, 46 of the rigid portion 20, 22. The stop 38 can be configured to limit movement of a liner 10 toward a distal end 42, 48 of the rigid portion 20, 22.

A rigid portion 21, 22 of a curved blade 101 can comprise a rigid portion formed of a rigid or a non-flexible material or a material having less flexibility than a flexible portion 23, 24 of the curved blade 101. A rigid portion 21, 22 can comprise a metal, a polymer, a ceramic, a carbon allotrope, e.g., graphene, or a combination of these. As shown in FIGS. 4 and 14, a rigid portion 21 can comprise a cutting window 49. A rigid portion 22 can comprise one or more cutting surfaces 50, such as a cutting edge or blade, serrations, burr or teeth. A cutting window 49 can be disposed adjacent to a distal end 48 of an inner member 12. A cutting surface 50 of the rigid portion 22 can be disposed adjacent to a distal end 48 of an inner member 12. The cutting window 49 and the cutting surface 50 can be configured to be aligned with one another when the inner member 12 is assembled with the outer member 11.

A curved blade 101 can comprise at least one flexible portion 23, 24 disposed adjacent to at least on rigid portion 19, 20, 21, 22. The flexible portion 24 of the inner member 12 can have a length 90 and can have an inner diameter 92 that cooperates with the inner diameter 32, 34, 56, 58 of the at least one rigid portion 20, 22 to define the lumen 18 of the inner member 12. The inner diameter 92 of the flexible portion 24 can be greater than the inner diameter 32, 34, 56, 58 of the at least one rigid portion 20, 22. The inner diameter 92 of the flexible portion 24 can be equal to, or essentially equal to, an inner diameter 32, 34, 56, 58 of the at least one rigid portion 20, 22. A flexible portion 23, 24 can be disposed adjacent to a first rigid portion 19, 20 and a second rigid portion 21, 22. The flexible portion 23, 24 can be disposed between a first rigid portion 19, 20 and a second rigid portion 21, 22. As shown in FIGS. 1, 2, 10 and 12, a flexible portion 23, 24 of the curved blade 101 can comprise a flexible material 26 such as can be configured to impart flexibility to the flexible portion 23, 24. The flexible material 26 can comprise one or more strips of a flexible material. The flexible material 26 can comprise one or more strips wound or wrapped around an axis A of the inner member 12. In an example in which the outer member 11 has a flexible portion 23, the flexible material 26 can comprise one or more strips of a flexible material wrapped around an axis A of the outer member 11. The one or more strips of flexible material 26 can be wound in a helical or spiral fashion around the axis A. The flexible material 26 can comprise a first strip of flexible material and a second strip of flexible material, the first strip wound or wrapped around the axis A of the inner member 12 in a first direction D1, and the second strip wound or wrapped over the first strip of flexible material 26 and around the axis A in a second direction D2 opposite the first direction D1. The flexible material 26 can comprise a first strip of flexible material 26, a second strip of flexible material 26, and a third strip of flexible material 25, 26, the first strip of flexible material wound or wrapped around the axis A of the inner member 12 in a first direction D1, the second strip wound or wrapped over the first strip and around the axis A in a second direction D2 opposite the first direction, and the third strip wound or wrapped over the second strip and around the axis A in the first direction D1. The flexible material 26 can comprise a plurality of strips of flexible material 26 that can be braided or interlocked with one another such as to form a flexible portion 23, 24 of a curved blade 101. As shown in FIGS. 1, 2, 10 and 12, the flexible portion 23, 24 can overlap the at least one rigid portion 19, 20, 21, 22. The flexible portion 23, 24 can overlap a first rigid portion 19, 20. The flexible portion 23, 24 can overlap a second rigid portion. The flexible portion 23, 24 can be affixed to the at least one rigid portion 19, 20, 21, 22. The flexible portion 23, 24 can be affixed to a first rigid portion 19, 20. The flexible portion 23, 24 can be affixed to a second rigid portion 21, 22. The flexible portion 23, 24 can be fixed, such as by a weld, an adhesive, or a fastener, to the at least one rigid portion 19, 20, 21, 22. The flexible portion 23, 24 can be affixed such as by a weld, an adhesive, or a fastener, to a first rigid portion 19, 20. The flexible portion 23, 24 can be affixed, such as by a weld, an adhesive, or a fastener to a second rigid portion comprising a blade portion 21, 22.

In FIGS. 1, 2 and 4, a liner 10 of a curved blade 101 can comprise a liner wall 70 defining a lumen 64, the liner wall 70 extending a length 82 between a liner proximal end 66 and a liner distal end 68. The liner 10 can be formed of a natural polymer or a synthetic polymer (e.g., Polyolefin, Polyvinyl Chloride, Polyether Block Amide, Thermoplastic Polyurethane, etc.), a fabric, or a combination of any of these materials. The liner 10 can be formed of any material configured to flex or bend. The liner 10 can be configured to flex, such as in response to or in coordination with flexing or bending of a flexible portion 23, 24 of the curved blade 101. The liner wall 70 can comprise a first outer diameter 72. The liner 10 can comprise a first outer diameter 72 and a second outer diameter 74 different from the first outer diameter 72. The liner 10 can comprise a first outer diameter 72 adjacent to a liner proximal end 66 and a second outer diameter 74 adjacent to a liner distal end 68. The second outer diameter 74 can be less than the first outer diameter 72.

A liner 10 can comprise a locking feature 78 configured to retain the liner 10 within a lumen 18 of the inner member 12. The locking feature 78 can comprise a flared region in the wall 70. The locking feature 78 can comprise a portion of the liner wall 70 having a first outer diameter 72. The locking feature 78 can comprise a portion of a wall 70 having a first outer diameter 72 disposed adjacent to a liner proximal end 74. The locking feature 78 can comprise one or more apertures or recesses formed in the liner wall 70. The locking feature 78 can comprise a projection extending from the wall 70. The locking feature 78 can comprise a flange. The locking feature 78 can extend around all or only a portion of the circumference of the liner wall 70. The locking feature 78 can be disposed at one or a plurality of discrete locations around the circumference or other periphery of the liner wall 70. A locking feature 78 can comprise a transition in the thickness 80 of the liner wall 70. The locking feature 78 can comprise a transition between a first outer diameter 72 and a second outer diameter 74 of a liner wall 70. A locking feature 78 can comprise a transition between a first thickness 80A of a liner wall 70 and a second thickness 80B of a liner wall 70 that is different from the first thickness 80A. A liner wall second thickness 80B can be less than the wall first thickness 80A. The locking feature 78 can comprise an annular ledge, such as can be formed by or on the liner wall 70. A locking feature 78 can comprise a liner end wall 76. A locking feature 78 can comprise an end wall 76 adjacent to the distal end 68 of the liner 10.

When at least one rigid portion 20, 22, and a flexible portion 24 are in an assembled configuration for the inner member 12, as shown in FIGS. 1, 2, 10, 11, and 16, a liner 10 can be inserted in a proximal to distal direction, through the lumen 18 of the inner member 12. In FIG. 1B, in a method of forming a curved blade 101, a liner 10 can be inserted into an assembled inner member 12 such as by inserting a liner 10 distal end 68 into at least one rigid portion 20, 22 of inner member 12 until the liner 10 engages an a stop 38 of the at least one rigid portion 20, 22. The liner 10 can be inserted into an assembled inner member 12 such as by inserting a liner 10 distal end 68 into the at least one rigid portion 20, pushing the liner 10 through the at least one rigid portion 20 until a locking feature 78 of the liner 10 engages a stop 38 of the at least one rigid portion 22. The liner 10 can be inserted into an assembled inner member 12 comprising at least one rigid portion 20 adjacent to a proximal end 14 of inner member 12, until a locking feature 78 of the liner 10 engages a stop 38 of the at least one rigid portion 20. The liner 10 can be inserted into an assembled inner member 12 comprising at least one rigid portion 22 adjacent to a distal end 16 of inner member 12 until a locking feature 78 of the liner 10 engages a stop 38 of an interior wall 28B, 52B of the at least one rigid portion 20, 22. The liner 10 can be inserted into the inner member 12 until the locking feature 78 engages an interior wall 28B, 52B of the inner member 12. The locking feature 78 can comprise an end wall 76 of a liner 10 and the liner 10 can be inserted until the liner end wall 76 engages an interior wall 28B, 52B of the inner member 12. A locking feature 78 can comprise an end wall 76 of a liner 10 and the liner 10 can be inserted until the liner end wall 76 engages an interior wall 52B adjacent to a distal end 16 of the inner member 12. The liner 10 can be inserted into an inner member 12 until the liner 10 is disposed at a predetermined position within the inner member 12. The predetermined position can be a position in which the locking feature 78 or end wall 76 of the liner 10 does not engage a stop 38 or an interior wall 28B, 52B of the inner member 12 and the liner 10 and/or the inner member 12 can subjected to a temperature or pressure (as described below) to cause the locking feature 78 or end wall 76 of the liner 10 to engage a stop 38 or the interior wall 28B, 52B of the inner member 12.

An inner member 12 can be inserted proximally to distally through a lumen 17 of the outer member 12. An inner member 12 can be inserted into an outer member 11 after the liner 10 is inserted into the inner member 12. An inner member 12 can be inserted into an outer member 11 before a liner 10 is inserted into the inner member 12. The inner member 12 can be inserted into a lumen 17 of the outer member 11 by inserting the distal end 16 of the inner member 12 through the proximal end 13 of the outer member 11, pushing the inner member 12 through the lumen 17 until the distal end 16 of the inner member 12 reaches the distal end 15 of the outer member 11. The inner member 12 can be inserted into the lumen 17 of the outer member 11 until a rigid portion 22 at distal end 16 of the inner member 12 reaches a rigid portion 21 at the distal end 15 of the outer member 11. An inner member 12 can be inserted into a lumen 17 of the outer member 11 until a cutting surface 50 of the inner member 12 is aligned with a cutting window 49 of the outer member 11.

In a fully assembled configuration, a curved blade 101 can comprise a liner 10 within a lumen 18 of the inner member 12. The liner 10 can be co-axial with an axis A of the inner member 12 of the curved blade 101. The liner 10 can have a length 82 that can be equal to, or substantially equal to, a length 62 of an inner member of the curved blade 101. The liner 10 can have a length 82 that is less than a length 62 of an inner member 12 of the curved blade 101. A liner 10 can have a length 82 that is less than a length 88 of an outer member 11 of the curved blade 101. The liner 10 can be disposed with the lumen 18 adjacent to a flexible portion 23, 24 of the curved blade 101. A liner 10 can be disposed adjacent to a flexible portion 24 of an inner member 12 of the curved blade 101. The liner 10 can have a length 82 that is equal to or greater than a length 90 of the flexible portion 24 of the inner member 12. The liner 10 can extend a length 82 such that the liner proximal end 66 is disposed adjacent to and/or overlaps a distal end 42 of the rigid portion 20 of inner member 12 of the curved blade 101. The liner 10 can extend a length 82 such that the liner distal end 76 is adjacent to and/or can overlap a proximal end 46 of a rigid portion 22 of the inner member 12 of the curved blade 101. The liner 10 can extend a length 82 such that a liner proximal end 66 overlaps a distal end 42 of a first rigid portion 20 of the inner member 12. The liner 10 can extend a length 82 such that liner distal end 68 is adjacent to and/or can overlap a proximal end 46 of a second rigid portion 22 of the inner member 12. The liner 10 can extend a length 82 such that a liner proximal end 66 overlaps a distal end 42 of a first rigid portion 20 and a liner distal end 68 overlaps a proximal end 46 of a second rigid portion 22 of an inner member 12 of a curved blade 101. The liner 10 can extend a length 82 such that a first locking feature 78 can engage a stop 38 of a first rigid portion 20 and a liner second locking feature 76, 78 can engage a stop 38 of a second rigid portion 22 of an inner member 12.

The liner 10 can have a length 82 that can extend substantially the length 62 of the inner member 12, but the length 82 can be such that it does not reach the cutting surface 50 of the inner member 12 and is not exposed by the cutting window 49 of the outer member 13.

Figure 16:
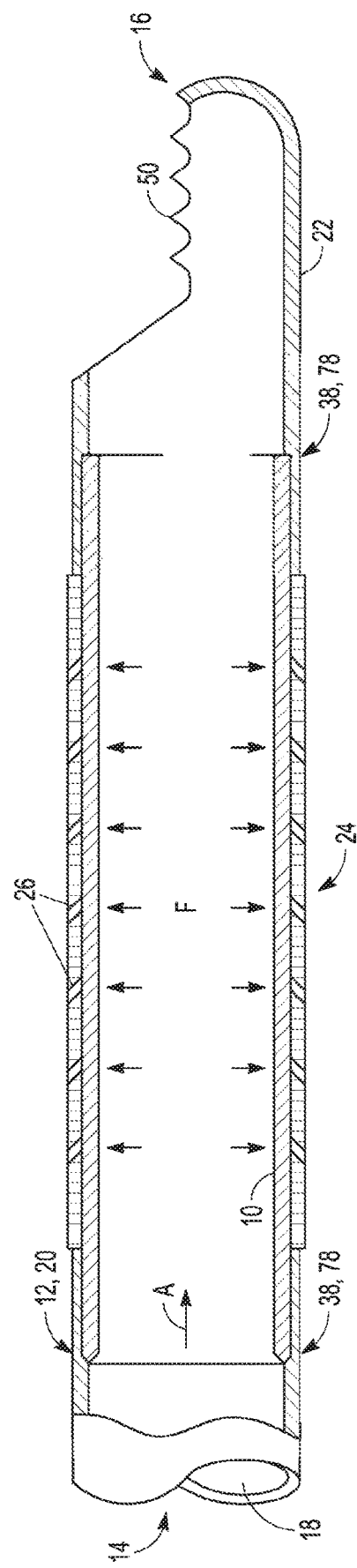
FIG. 16 illustrates a cross-sectional view of an inner member and liner of a curved blade, in an assembled configuration, showing the application of heat and/or pressure (F) to expand the liner within the inner member, or allowing a cooled liner to warm to room temperature to expand within the inner member, to form a seal between the liner and the inner member.

A method of forming a curved blade 101 can comprise sealing a lumen 18 of an inner member 12 of the curved blade 101. The method of forming a curved blade 101 can comprise forming a seal S between a lumen 18 and a flexible portion 24 of an inner member 12. In FIG. 16, a liner 10 can be configured to provide a seal S to a lumen 18 of the curved blade 101. The liner 10 can be configured to seal S a lumen 18 of an inner member 12 of a curved blade 101. The liner 10 can be configured to form a seal S between liner wall 70 and a flexible portion 24 of an inner member 12 of a curved blade 101. The liner 10 can be configured to form a seal S by causing a liner outer diameter 72, 74 to expand to meet an inner diameter 92 of the flexible portion 24 of the inner member 12 of a curved blade 101. The seal S can be imparted to an assembled combination of an inner member 12 comprising at least one rigid portion 20, 22 and a flexible portion 24, and a liner 10, by subjecting the inner member 12 to a pressure. The seal S can be imparted by applying pressure in the form of a fluid F (gas or liquid) to the liner 10 and the lumen 18 of the inner member 12 of a curved blade 101 (either when separated from the outer member H or when assembled with the outer member 11) and sealing the proximal end 14 and sealing the distal end 16 of the inner member 12, e.g., by providing a cap or a cover for the proximal end 14 and/or the distal end 16, or by wrapping, encasing or closing the proximal end 14 and/or the distal end 16 with a material configured to seal the proximal end 14 and/or the distal end 16. The seal S can be imparted by applying a fluid F to the liner 10 and the lumen 18 of the inner member 12 of a curved blade 101, sealing the proximal end 14 and sealing the distal end 16 of the inner member 12, and subjecting the inner member 12 (either when separated from the outer member 11 or when assembled with the outer member 11) and fluid F to a temperature above 25° C. The temperature above 25° C. can be a predetermined temperature. In an aspect, a temperature above 25° C. can be any temperature from about 50° C. to about 80° C. In a preferred aspect, a temperature above 25° C. can be any temperature from about 60° C. to about 70° C. In an aspect, a seal S can be imparted by applying a cooling temperature, e.g. a temperature below 45° C., to a liner 10, inserting the cooled liner 10 into the assembled inner member 12 (either when the inner member 12 is separated from the outer member 11 or when the inner member 12 is assembled with the outer member 11), and allowing the liner 10 to warm to a temperature such that the liner 10 outer diameter 72, 74 expands to meet an inner diameter 32, 34, 56, 58, 92 the rigid portion 20, 22, and/or the flexible portion 24 of the inner member 12. In an aspect, a cooling temperature can be any temperature from about 0° C. to about 45° C. In a preferred aspect, a cooling temperature can be any temperature from about 15° to about 25° C. In an aspect, the liner 10 is comprised of a material that will not revert to an original liner outer diameter after the foregoing manipulations of the liner 10 to form a seal S.

A method of performing a surgical procedure with a curved blade 101, as shown in FIG. 1B, can include inserting a surgical tool into a passage of a patient. The surgical tool can include a curved blade 101 comprising an inner member 12 and an outer member 11 each having a proximal end 13, 14 and distal end 15, 16. The inner member 12 can include a cutting surface 50 adjacent to the distal end 16 and at least one flexible portion 24 disposed between the proximal end 14 and the distal end 16. The outer member can include a cutting window 49 disposed adjacent to the distal end 15 and at least one flexible portion 23 disposed between the proximal end 13 and the distal end 15. The inner member 12 can be received within the outer member 11 in a manner to align the cutting surface 50 of the inner member 12 with the cutting window 49 of the outer member 11. A liner 10, disposed within a lumen 18 of the inner member 12, can have a proximal end 66 and a distal end 68. A proximal end 66 of the liner can have a locking feature 78 engaged with a stop 38 adjacent to a proximal end 14 of the inner member 12. A distal end of the liner 10 can have a locking feature 76, 78 at a distal end 68, the locking feature 76, 78 engaged with a stop 38 adjacent to a distal end 16 of the inner member 12. The method of performing a surgical procedure with a surgical tool comprising a curved blade 101 can include inserting the curved blade 101 into the passage of the patient and allowing an inner member 12 to rotate or oscillate with respect to the outer member 11. The method of performing a surgical procedure with a surgical tool comprising a curved blade 101 can include removing the surgical tool from the passage of the patient.

The foregoing description has been provided for purposes of illustration and description. It is not intended to be exhaustive or to restrict or limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The above detailed description includes references to the accompanying drawings, which form a part of the detailed description. The drawings show, by way of illustration, specific aspects in which the invention can be practiced. These aspects are also referred to herein as "embodiments" or "examples." Such examples can include elements in addition to those shown or described. However, the present inventors also contemplate examples in which only those elements shown or described are provided. Moreover, the present inventors also contemplate aspects using any combination or permutation of those elements shown or described (or one or more aspects thereof), either with respect to a particular example (or one or more aspects thereof), or with respect to other examples (or one or more aspects thereof) shown or described herein.

In this document, terminology used herein is for the purpose of describing particular example embodiments only and is not intended to be limiting. As used herein, the singular forms "a," "an," and "the" may include the plural forms as well, unless the context clearly indicates otherwise. The terms "a" or "an" are also used, as is common in patent documents, to include one or more than one, independent of any other instances or usages of "at least one" or "one or more." in this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in this document, including in the following claims, the terms "including," "comprising" and "having" are open-ended and inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

Although the terms "first," "second," "third," etc. may be used herein to describe various elements, components, regions, layers and/or sections, these elements, components, regions, layers and/or sections should not be limited by these terms. These terms may be only used to distinguish one element, component, region, layer or section from another region, layer or section. Thus, a first element, component, region, layer or section discussed below could be termed a second element, component, region, layer or section without departing from the teachings of the example embodiments. Moreover, in the following claims, the terms "first," "second," and "third," etc. are used merely as labels, and are not intended to impose numerical requirements on their objects. Terms such as "first," "second," "third," and other numerical terms used herein, including the following claims, do not imply a sequence or order unless clearly indicated by the context.

In this disclosure, relative terms, such as, for example, "about", "generally", or "substantially" are used to indicate a possible variation of ±10% in a stated numeric value or within ±10° of the numeric value.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations.

The scope of the invention should be determined with reference to the appended claims, along with the full scope of equivalents to which such claims are entitled.

What is claimed is:

1. A device for cutting bone or tissue, the device comprising:
   an outer member defining a lumen and comprising a cutting window;
   an inner member configured to be disposed within the lumen of the outer member, the inner member comprising a cutting surface, at least one rigid portion, and at least one flexible portion; and
   a liner disposed within a lumen of the at least one flexible portion, the liner extending a length of the at least one flexible portion, the liner comprising an outer wall having a locking feature configured to engage an inner wall of the at least one rigid portion to retain the liner at a predetermined position within the lumen of the at least one flexible portion.

2. A device for cutting bone or tissue, the device comprising:
   an outer member defining a lumen and comprising a cutting window;
   an inner member configured to be disposed within the lumen of the outer member, the inner member comprising a cutting surface, at least one rigid portion, and at least one flexible portion; and
   a liner configured to be disposed within a lumen of the inner member, the liner comprising an outer wall having a locking feature configured to engage an inner wall of the at least one rigid portion to retain the liner at a predetermined position within the lumen of the inner member, wherein the locking feature comprises an end wall of the liner.

3. A device for cutting bone or tissue, the device comprising:
an outer member defining a lumen and comprising a cutting window;
an inner member configured to be disposed within the lumen of the outer member, the inner member comprising a cutting surface, at least one rigid portion, and at least one flexible portion; and
a liner configured to be disposed within a lumen of the inner member, the liner comprising an outer wall having a locking feature configured to engage an inner wall of the at least one rigid portion to retain the liner at a predetermined position within the lumen of the inner member, wherein the locking feature comprises a flared region of the liner outer wall or a projection extending from the liner outer wall.

4. The device of claim 1, wherein the inner wall comprises a stop configured to engage the locking feature to retain the liner at the predetermined position.

5. The device of claim 4, wherein the stop is disposed adjacent to a distal end of the at least one rigid portion.

6. The device of claim 4, wherein the stop is disposed adjacent to a proximal end of the at least one rigid portion.

7. The device of claim 1, wherein the lumen of the inner member comprises a first inner diameter and a second inner diameter, the second inner diameter being different from the first inner diameter, and wherein the locking feature is configured to engage the inner wall at a transition between the first inner diameter and the second inner diameter.

8. The device of claim 1, wherein the inner wall comprises a first thickness and a second thickness, the second thickness being different from the first thickness, and wherein the locking feature is configured to engage the inner wall at a transition between the first thickness and the second thickness of the inner wall.

9. The device of claim 1, wherein the at least one rigid portion comprises a first rigid portion and a second rigid portion axially spaced from the first rigid portion, wherein the first rigid portion comprises a first inner wall and the second rigid portion comprises a second inner wall, and wherein the locking feature comprises a first locking feature configured to engage the first inner wall of the first rigid portion and a second locking feature configured to engage the second inner wall of the second rigid portion.

10. The device of claim 1, wherein the locking feature is configured to engage a recess or aperture in the inner wall of the at least one rigid portion.

11. The device of claim 1, wherein the inner wall comprises a recess or aperture configured to engage the locking feature.

12. The device of claim 1, wherein the predetermined position is adjacent to the at least one flexible portion.

13. The device of claim 1, wherein the liner is configured to engage the inner wall of the at least one rigid portion to form a seal between the liner and the inner member.

* * * * *